United States Patent [19]

Baillie et al.

[11] 4,339,443
[45] Jul. 13, 1982

[54] COMPOUNDS AND COMPOSITIONS

[75] Inventors: Alister C. Baillie, Cambridge; Brian J. Wright, Bishops Stortford; Kenneth Wright, Cambridge, all of England

[73] Assignee: FBC Limited, Cambridge, England

[21] Appl. No.: 70,440

[22] Filed: Aug. 28, 1979

[30] Foreign Application Priority Data

Sep. 22, 1978 [GB] United Kingdom ............... 37723/78
Nov. 18, 1978 [GB] United Kingdom ............... 45140/78

[51] Int. Cl.³ .................... A01N 57/20; A01N 57/24; C07F 9/30; C07F 9/65
[52] U.S. Cl. .................... 424/200; 544/232; 548/111; 549/5; 549/221; 260/239 BC; 260/465.8 R; 260/502.4 R; 260/502.5; 260/501.21; 260/456 R; 260/923; 260/944; 260/945; 260/948; 260/949; 260/950; 260/951; 260/938; 260/940; 260/935; 424/201; 424/203; 424/214; 424/217
[58] Field of Search ............... 260/502.4 R, 923, 944, 260/945, 946, 948, 949, 950, 951, 239 BC, 502.5, 501.21, 461.8 R, 340.7, 340.9 R, 456 R; 549/5; 548/111; 544/232; 424/200, 202, 203, 214, 216, 217

[56] References Cited

U.S. PATENT DOCUMENTS 2,629,731 2/1953 Harman .................... 260/502.4 R
2,900,408 8/1959 Blaser et al. .................... 260/946
2,956,919 10/1960 Baker et al. .................... 260/946
3,053,876 9/1962 Malz et al. .................... 260/944

Primary Examiner—Anton H. Sutto
Attorney, Agent, or Firm—Morgan, Finnegan, Pine, Foley & Lee

[57] ABSTRACT

There are described pesticidal compositions comprising one or more compounds of the formula I,

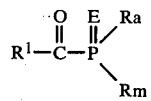

in which
Ra is a group $R^2$ or $-OR^2$,
E is oxygen or sulphur,
Rm is $-O^{\ominus}M^{\oplus}$ or $-NRyRz$,
$M^{\oplus}$ is one equivalent of an agriculturally acceptable cation,
$R^1$ and $R^2$, which may be the same or different, each represent hydrogen, alkyl, alkenyl, alkynyl or aryl; the alkyl, alkenyl, alkynyl or aryl optionally being substituted by one or more halogen, alkoxy, nitro, alkyl, $-CF_3$, nitrile, or carboxylic acid or a salt, ester, or amide thereof, and
Ry and Rz, which may be the same or different, each represent hydrogen or alkyl,
or an agriculturally acceptable derivative thereof.
There are also described methods for making and using compounds of formula I.

9 Claims, No Drawings

COMPOUNDS AND COMPOSITIONS

This invention concerns herbicidal, fungicidal or insecticidal compositions, new herbicidally, fungicidally or insecticidally active compounds, and processes for the preparation of such compounds.

In one aspect, this invention provides a pesticidal composition comprising one or more compounds of the formula I,

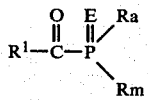

in which
Ra is a group $R^2$ or $-OR^2$
E is oxygen or sulphur,
Rm is $-O^\ominus M^\oplus$ or $-NRyRz$,
$M^\oplus$ is one equivalent of an agriculturally acceptable cation,
$R^1$ and $R^2$, which may be the same or different, each represent hydrogen, alkyl, alkenyl, alkynyl or aryl; the alkyl, alkenyl, alkynyl or aryl optionally being substituted by one or more halogen, alkoxy, nitro, alkyl, $-CF_3$, nitrile or carboxylic acid or a salt, ester or amide thereof, and
Ry and Rz, which may be the same or different, each represent hydrogen or alkyl,
or an agriculturally acceptable derivative thereof.

In another aspect this invention provides a method of combating pests, e.g. weeds, fungi or insects, at a locus either infested with pests or liable to infestation therewith, which method comprises applying to the locus a pesticidally effective amount of one or more compounds of formula I, or of an agriculturally acceptable derivative thereof.

According to the invention we also provide as new compounds the compounds of formula I, and agriculturally acceptable derivatives thereof, with the proviso that when $R^1$ is methyl and Ra is methoxy then $M^\oplus$ is other than sodium.

We prefer Rm to be $-O^\ominus M^\oplus$.

$M^\oplus$ may be a tri-, or preferably a di- or mono-valent cation. We prefer $M^\oplus$ to be an alkali metal (e.g. sodium or lithium), an alkaline earth metal (e.g. magnesium or calcium), or the ammonium ($NH_4^\oplus$) cation or a protonated primary, secondary or tertiary-amine (e.g. a primary, secondary or tertary alkylamine in which each alkyl group contains 1 to 16 carbon atoms) or a quaternary (e.g. a quarternary alkyl C 1 to 16) ammonium cation. $M^\oplus$ may also be a herbicidally active cation, e.g. the cation of paraquat, difenzoquat or a triazolium compound such as is disclosed in Belgian Patent Specification No. 848,615. We particularly prefer $M^\oplus$ to be sodium.

Ra is preferably a group $R^2$ and more preferably is hydrogen or methyl.

When $R^1$ or $R^2$ are optionally substituted alkyl, alkenyl or alkynyl they preferably contain up to 10, more preferably up to 6 and most preferably up to and including 3 carbon atoms. When $R^1$ or $R^2$ themselves carry a substituent group that group preferably contains up to 6 carbon atoms. When $R^1$ or $R^2$ is an aryl group we prefer it to be a phenyl group. We also prefer E to be oxygen. Ry and Rz preferably contain up to 10 and more preferably up to 6 carbon atoms.

When $R^1$ or $R^2$ represent a group substituted by a carboxylic acid group, the carboxylic acid may be in the form of an agriculturally acceptable salt, ester or amide thereof. Suitable salts include those having a cation $M^\oplus$ as described above. Suitable esters include C 1 to 10 esters, e.g. C 1 to 10 alkyl esters, and suitable amides include those derived from ammonia or from a mono- or di-alkyl or aryl-, (e.g. phenyl-) amine.

As a specific group of compounds we provide compounds of formula I in which $R^1$ is hydrogen, alkyl C 1 to 3, or $-CH_2CH_2COOH$ or a salt or C 1 to 6 alkyl ester thereof, Ra is hydrogen, alkyl C 1 to 6, phenyl, hydroxy or alkoxy C 1 to 6 and $M^\oplus$ is sodium or lithium. As a further specific group we provide compounds of formula I in which $R^1$ is methyl or $-CH_2CH_2COOH$ or a salt or C 1 to 6 alkyl ester thereof, Ra is methyl and $M^\oplus$ is sodium.

We particularly prefer the compound of Example 8 and the agriculturally acceptable derivatives, and especially the ketals, thereof, e.g. the compounds of Example 17 and 18.

Agriculturally acceptable derivatives of the compounds of formula I include derivatives of the $-CO-$ group. More particularly there may be mentioned acetals or ketals, e.g. derived from a C 1 to 10, preferably a C 1 to 8, alkanol, such as methanol, ethanol or propanol or from ethylene glycol or from 1,2-dimethyl ethylene glycol, or from an aryl substituted alkanol such as benzyl alcohol; hydrazones, e.g. derived from hydrazine or a substituted hydrazine such as a phenylhydrazine especially 2,4-dinitrophenyl hydrazine; oximes and oxime derivatives such as oxime esters, or ethers, e.g. oxime C 1 to 6 alkyl ethers or the oxime benzyl ether; bisulphite addition compounds, Schiff's bases, cyanohydrins and their derivatives (e.g. esters and ethers including trialkyl silyl ethers), semicarbazones, thiosemicarbazones, hemithioketals, thioketals, imidazolidines, oxazolidines, thiazolidines, perhydro-1,3-diazines, perhydro-1,3-thiazines and perhydro-1,3-oxazines.

A particular group of agriculturally acceptable derivatives of compounds of formula I are those of formula Ia,

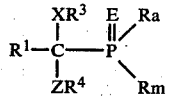

in which
$R^1$, E, Ra and Rm are as defined above,
X and Z, which may be the same or different, each represent oxygen, sulphur or a group $-NR^5-$,
$R^5$ represents hydrogen, alkyl, e.g. containing 1 to 10 carbon atoms or aryl, e.g. phenyl,
$R^3$ and $R^4$, which may be the same or different each represent alkyl, or aryl (e.g. phenyl) each of which may optionally be substituted by hydroxy, alkoxy, alkyl, halogen, carbonyl oxygen or alkoxycarbonyl; or $R^3$ and $R^4$ together form alkylene (e.g. propylene, ethylene or 1,2-dimethylethylene), or arylene (e.g. o-phenylene), each of which may optionally be substituted by hydroxy, alkoxy, alkyl, halogen, carbonyl oxygen or alkoxycarbonyl,
or $XR^3$ and $ZR^4$ together form $=C(CN)_2$ or $=NR^{10}$ in which $R^{10}$ represents alkoxy C 1 to 6, benzyloxy, hydroxy, phenyl, $-NH$ phenyl, $-NH-(2,4$-dinitrophenyl), $-NHCONH_2$ or $-NHCSNH_2$, or one of XR$^3$ and ZR$^4$ is —OH (or esters or ethers thereof) and the other is —CN or —SO$_3^\ominus$M$^\oplus$.

Should XR$^3$ and ZR$^4$ together form carbonyl oxygen the compounds of formula Ia will be compounds of formula I.

A further group of agriculturally acceptable derivatives of compounds of formula I are the enol ethers, enol esters and enol thioethers of the compounds of formula I, e.g. compounds of formula Ib, $$\text{(RyRz)C}=\overset{\overset{Q}{|}}{C}-\overset{\overset{E}{\|}}{P}\diagdown\overset{Ra}{\diagup}_{Rm} \qquad \text{Ib}$$

in which
Ra, E, Ry, Rz and Rm are as defined above,
Q represents a group —OR$^6$ or S(O)$_n$R$^7$,
n is 0, 1 or 2,
R$^6$ is alkyl or acyl, (e.g. alkanoyl), and
R$^7$ is alkyl or aryl, e.g. phenyl.

We prefer -XR$^3$ and -ZR$^4$, when they are separate, each to contain up to and including 10, and preferably up to and including 6 carbon atoms. When R$^3$ and R$^4$ together form an optionally substituted alkylene or arylene chain we prefer the combined R$^3$ and R$^4$ group to contain up to and including 15, preferably up to and including 8 and more preferably 2, 3 or 4 carbon atoms. When R$^3$ and R$^4$ together form a chain we prefer at least one of X and Z to be a group —NR$^5$—. We also prefer the group Q to contain up to and including 10, and more preferably up to and including 6 carbon atoms.

According to the invention we also provide a process for the production of a compound of formula I, and in particular the new compounds of formula I, or an agriculturally acceptable derivative thereof, which comprises (a) producing a compound of formula I, or an agriculturally acceptable derivative thereof, in which Rm is —O$^\ominus$M$^\oplus$ by reacting a compound of formula II, $$R^1-\overset{\overset{O}{\|}}{C}-\overset{\overset{E}{\|}}{P}\diagdown\overset{Ra}{\diagup}_{ORb} \qquad \text{II}$$

or a suitable derivative thereof, in which R$^1$, Ra and E are as defined above, and Rb is alkyl, with a compound of formula III, $$\text{MY} \qquad \text{III}$$

in which M is as defined above and Y is an anion, or (b) producing a compound of formula I, or an agriculturally acceptable derivative thereof, in which Ra is —OH, by replacing with hydrogen a group Rb in a compound of formula IV, $$R^1-\overset{\overset{O}{\|}}{C}-\overset{\overset{E}{\|}}{P}\diagdown\overset{ORb}{\diagup}_{O^\ominus M^\oplus} \qquad \text{IV}$$

or a suitable derivative thereof, in which R$^1$, Rb, E and M are as defined above, (c) producing a compound of formula I, or an agriculturally acceptable derivative thereof, in which R$^1$ or R$^2$ represents alkyl, alkenyl, alkynyl or aryl substituted by a carboxylic acid group, by selective cleavage of a corresponding compound of formula I, or a suitable derivative thereof, in which R$^1$ or R$^2$ represents alkyl, alkenyl, alkynyl or aryl substituted by nitrile, a carboxylic acid ester or amide, (d) producing a compound of formula I, or an agriculturally acceptable derivative thereof, in which Rm is —NRyRz by reacting a compound of formula VIII, $$R^1-\overset{\overset{O}{\|}}{C}-\overset{\overset{E}{\|}}{P}\diagdown\overset{Ra}{\diagup}_{Hal} \qquad \text{VIII}$$

or a suitable derivative thereof, in which R$^1$, E and Ra are as defined above, and Hal represents halogen, with an amine NHRyRz, or (e) converting a compound of formula I to an agriculturally acceptable derivative thereof, or vice versa, or converting one agriculturally acceptable derivative of a compound of formula I to another.

The reaction of process (a) is preferably carried out in a solvent which is inert under the reaction conditions, e.g. a ketone such as acetone or ethyl methyl ketone. The reaction is preferably carried out at an elevated temperature, e.g. of from 50 to 150° C. and especially at the reflux temperature of the solvent. The reaction of process (a) may be carried out using the compound of formula II itself or a suitable derivative thereof. We prefer the anion Y to be a good nucleophile, e.g. an iodide, bromide, ethanemercaptide, methanemercaptide or benzenemercaptide anion.

When a derivative, e.g. a ketal, of the compound of formula II is used the anion Y may, in addition to those defined above, be the hydroxy anion, e.g. the compound of formula III may be sodium hydroxide, and the reaction may be carried out in an aqueous medium.

Suitable derivatives of the compound of formula II include those of formula IIa, $$R^1-\overset{\overset{XR^3}{|}}{\underset{\underset{ZR^4}{|}}{C}}-\overset{\overset{E}{\|}}{P}\diagdown\overset{Ra}{\diagup}_{ORb} \qquad \text{IIa}$$

in which Ra, Rb, R$^1$, R$^3$, R$^4$, E, X and Z are as defined above.

The reaction of process (b) may conveniently be carried out by subjecting a solution of the starting material to an elevated temperature, e.g. of from 80° to 120° C., for example in formic acid.

In process (c) care should be taken to ensure that the cleavage does not degrade other parts of the molecule. When an alkyl ester is used as starting material the cleavage may be effected by means of, for example, lithium iodide. The reaction is preferably carried out in a solvent which is inert under the reaction conditions and at a temperature of from about 20° to 150° C.

Process (d) may be carried out in a solvent which is inert under the reaction conditions or in an excess of the amine HNRyRz. The reaction may be carried out at a temperature of from about 0° to 60° C. Suitable derivatives for use in this process are those of formula IIa in which —ORb is replaced by Hal.

Process (e) may comprise conversion of a derivative of a compound of formula I, e.g. a compound of formula Ia, to a compound of formula I. Such a conversion may be effected by hydrolysis, e.g. under acidic conditions, using for example aqueous acetic or formic acid. The reaction is preferably carried out at a temperature of from about 0° to 100° C. The conversion of a derivative to a compound of formula I according to process (e) may be carried out sequentially with the reaction of process (a), i.e. process (a) in which the compound of formula II is used in the form of a derivative thereof, followed by process (e).

Process (e) may also comprise conversion of a compound of formula I to an agriculturally acceptable derivative thereof, e.g. to a compound of formula Ia. Thus the process may comprise reaction of a compound of formula I with an appropriate alcohol, amine, thiol, malononitrile, an alkoxyamine, an aralkyloxyamine, e.g. benzyloxyamine, hydroxylamine, hydrazine, an optionally substituted phenylhydrazine, semicarbazide, thiosemicarbazide or a cyanide. The conversions may be carried out under conditions, and using reagents, which are conventional for the conversion of carbonyl oxygen to the appropriate derivative. When an oxime is to be produced alkoxy exchange may take place when an alkanol solvent is used. Thus use of methoxyamine starting material may yield an O-ethyloxime product when ethanol is used as solvent.

As a further facet process (e) may comprise production of an enol ether of formula Ib by methods known per se, e.g. by pyrolysis (for example at 150° to 300° C.) of a corresponding ketal of formula IIa in which $XR^3$ and $ZR^4$ are both alkoxy, and reaction of the resulting phosphinate ester with a compound of formula III.

Compounds of formula II are either known or may be made from known compounds using techniques known per se, e.g. by reaction of a compound of formula V, $$R^1COHal \qquad V$$

in which $R^1$ is as defined above, and
Hal is a halogen atom,
with a compound of formula VI, $$RxP(ORb)_2 \qquad VI$$

in which Rb is as defined above, and
Rx has the same significances as Ra save that it cannot be hydrogen or hydroxy.

Compounds of formula VI may be made from known compounds using techniques known per se.

Compounds of formula IIa may be made by reacting a compound of formula VII,

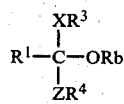

in which Rb, $R^1$, $R^3$, $R^4$, X and Z are as defined above, with $PCl_3$ or a compound of formula $RxPCl_2$, in which Rx is as defined above.

Compounds of formula VIII may be made using techniques known per se, e.g. conversion of a compound of formula I, or a derivative thereof, in which Rm is —O⊖M⊕ to a corresponding compound in which Rm is —OH, e.g. by column chromatography, and reaction of the —OH compound with, for example, thionyl chloride.

The compounds and compositions of the invention possess herbicidal and/or plant growth regulant or retardant activity, especially when employed pre- or preferably post-emergence, mainly against grass weeds such as ryegrass (*Lolium perenne*), black grass (*Alopecurus myosuroides*), barnyard grass (*Echinochloa crusgalli*), wild oats (*Avena fatua*), crabgrass (*Digitaria sanguinalis*), pig weed (*Amaranthus retroflexus*), pale persicaria (*Polygonum lapathifolium*), couch grass (*Agropyron repens*) purple nutsedge (*Cyperus rotundus*), yellow nudsedge (*Cyperus esculentus*) and Johnson grass (*Sorghum halepense*). Peas (*Pisum sativum*) and some other dicotyledonous crops such as soya beans (Glycine species), alfalfa and beans of the Vicia and Phaseolus genus, are tolerant to doses which are effective against such weeds, and the compounds and compositions are therefore of use in controlling the above weeds in peas and some other dicotyledonous crops.

The compounds and compositions of the invention are also of use in increasing the tillering of, or producing shorter or stronger stems in, cereals such as wheat (*Triticum aestivum*) and barley (*Hordeum vulgare*).

The compounds and compositions of the invention are also of use in industrial weed control, e.g. on railway tracks, and for directed spray application to high standing crops such as cotton, maize, tobacco, sugar cane, orchards, vineyards and in rubber, cocoa, tea, coffee and palm plantations.

The compounds and compositions of the invention are also active against a range of fungal diseases, particularly those of plants, such as *Phytophthora infestans* (potato blight), *Erysiphe graminis* (barley powdery mildew), *Puccinia recondita* (wheat brown rust), *Pyricularia oryzae* (rice blast), and *Plasmopara viticola* (vine downy mildew).

The compounds of formula I, and the agriculturally acceptable derivatives thereof, are preferably employed in the form of a composition containing a carrier and/or a surface active agent. When used in pre-emergent treatments the compounds are preferably applied as a surface spray.

The compositions may be prepared by admixing the ingredients. Usually the compositions are initially produced in the form of concentrates, e.g. containing 0.5–85% of the present compounds, and these are diluted with water or hydrocarbon, usually water, for application, generally such that the concentration of the compounds is 0.05–5%, percentages and parts in this specification being by weight unless otherwise indicated.

The carrier may be a liquid, e.g. water (e.g. water used to dilute a concentrate for application). If water is employed as carrier in a concentrate, an organic solvent may also be present as carrier, though this is not usually employed. A surface active agent may advantageously be present.

Those compounds soluble in water may be used as aqueous solutions with or without a surface active agent.

The carrier may be a liquid other than water, for example an organic solvent, such as a water immiscible solvent, e.g. a hydrocarbon which boils within the range 130°–270° C., in which the compound is dissolved or suspended. A concentrate containing a water immiscible solvent suitably also contains a surface active agent so that the concentrate acts as a self-emulsifiable oil on admixture with water. The liquid may be a water-miscible solvent e.g. 2-methoxy ethanol, methanol, propylene glycol, ethylene glycol, diethylene glycol, diethylene glycol monoethyl ether, formamide or methylformamide.

The carrier may be a solid, which may be finely divided. Examples of suitable solids are limestone, clays, sand, mica, chalk, attapulgite, diatomite, perlite, sepiolite, silicas, silicates, lignosulphonates and solid fertilizers. The carrier can be of natural or synthetic origin or can be a modified natural material.

Wettable powders soluble or dispersible in water may be formed by admixing the compound in particulate form with a particulate carrier or spraying molten compound on to the particulate carrier, admixing a wetting agent and a dispersing agent and finely grinding the whole powder mixture.

An aerosol composition may be formed by admixing the compound with a propellant e.g. a polyhalogenated alkane such as dichlorodifluoromethane, and suitably also with a solvent.

A flowable suspension concentrate may be formed by grinding substantially water insoluble compounds with water, a wetting agent and a suspending agent.

Thus the present composition can for example be solid (e.g. dust or granules) and contain a solid carrier or liquid (e.g. an emulsifiable concentrate) and contain a liquid carrier which is a hydrocarbon which boils within the range 130°–270° C.

The term 'surface active agent' is used in the broad sense to include materials variously called emulsifying agents, dispersing agents and wetting agents. Such agents are well known in the art.

The surface active agents used may comprise anionic surface active agents, for example soaps, mono- or di-esters of phosphoric acid with fatty alcohol ethoxylates or salts of such esters, fatty alcohol sulphates such as sodium dodecyl sulphate, sodium octadecyl sulphate or sodium cetyl sulphate, ethoxylated fatty alcohol sulphates, ethoxylated alkylphenol sulphates, lignin sulphonates, petroleum sulphonates, alkyl-aryl sulphonates such as alkyl-benzene sulphonates or lower alkylnaphthalene sulphonates e.g. butyl-naphthalene sulphonate, salts of sulphonated naphthaleneformaldehyde condensates, salts of sulphonated phenolformaldehyde condensates, or more complex sulphonates such as the amide sulphonates e.g. the sulphonated condensation product of oleic acid and N-methyl taurine or the dialkyl sulphosuccinates e.g. the sodium sulphonate of dioctyl succinate. Ionic surface active agents may tend to result in precipitation if employed in some formulations with certain of the compounds of the invention. Any surface active agent should be so chosen of course as to avoid this for any particular formulation envisaged.

The surface active agents may also comprise non-ionic agents, for example condensation products of fatty acid esters, fatty alcohols, fatty acid amides or fatty-, alkyl- or alkenyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quaternary ammonium compounds such as cetyl trimethyl-ammonium bromide or ethoxylated tertiary fatty amines.

Preferred surface active agents include ethoxylated fatty alcohol sulphates, lignin sulphonates, alkyl-aryl sulphonates, salts of sulphonated naphthalene-formaldehyde condensates, salts of sulphonated phenol-formaldehyde condensates, dialkyl sulphosuccinates, alkyl phenol ethoxylates, and fatty alkyl ethoxylates.

Non-ionic surface active agents are preferred.

Higher quantities of surface active agent, e.g. 5–50% of concentrate, than is normally present in commercial pesticidal or plant growth regulant compositions have been found to increase considerably the activity of the present compounds, even in some cases to several times the original activity.

The surface active agent employed to produce this potentiating effect may be selected from those described above. It is preferably a non-ionic surface active agent, especially an alkyl-substituted phenol condensed with ethylene oxide, e.g. tributylphenol condensed with 11 moles of ethylene oxide (available under the trade mark Sapogenat T110). The potentiating surface active agent may be admixed with the present compound for instance at the point of use, e.g. in a spray tank, or before, e.g. in a concentrate. Preferably the amount of potentiating surface active agent applied in a spray of the present compound is 0.1–5%, especially 1%.

The present active compound may be admixed with another pesticide, e.g. herbicide, insecticide or fungicide, or with a plant growth regulant. The invention provides a one pack presentation, in which the present compound is already mixed with another pesticide or plant growth regulant, and also a single package designed to hold the present compound and other pesticide or the plant growth regulant in separate containers, for mixing, e.g. in a spray tank, for application. Particular advantages are obtained with mixtures with another pesticide. The present compound may be used sequentially with another pesticide or plant growth regulant particularly with another fungicide or herbicide.

The herbicide may be for example one or more of a phenoxyaliphatic acid, substituted urea, triazine, phenol, nitrile, bypyridylium compound, substituted benzoic acid, halogenated aliphatic acid, carbamate, thiocarbamate, chloroacetamide, diazine or arsenic herbicide. In respect of selective herbicidal compositions for post-emergence use, the present compound may be used in admixture with for example a substituted phenoxyaliphatic acid; in respect of selective herbicidal compositions for pre-emergence use, the present compound may be used in admixture with for example a substituted urea, triazine, S-2,3-dichloroallyl di-isopropylthiocarbamate or S-2,3,3-trichloroallyl di-isopropylthiocarbamate.

The phenoxyaliphatic acid generally comprises alkyl and/or halogen substituted phenoxyaliphatic acids, and their salts, for example alkali metal, amine and alkanolamine salts, and functional derivatives, for example esters and amides. These compounds may be of activity such that they are recognised as commercial herbicides, or may be of only slight herbicidal activity. Examples of the substituted phenoxyaliphatic acids which may be mentioned include 2,4-dichlorophenoxyacetic acid, 2-(2,4-dichlorophenoxy)propionic acid, 2-methyl-4-chlorophenoxyacetic acid, 2,4,5-trichlorophenoxyacetic acid, gamma-2,4-dichlorophenoxybutyric acid, gamma-2-methyl-4-chloro-phenoxybutyric acid, alpha-2-methyl-4-chlorophenoxypropionic acid, 2-(4-[2,4-dichlorophenoxy]phenoxy)propionic acid and 2-(4-[4-chlorophenoxy]phenoxy)propionic acid.

The substituted urea generally comprises a tri- or tetrasubstituted urea such as N'-(3-chloro-4-methoxyphenyl)-N,N-dimethylurea, N'-(3-chloro-4-methylphenyl)-N,N-dimethylurea, N'-para-chlorophenyl-N,N-dimethylurea, N-butyl-N'-(3,4-dichlorophenyl)-N-methylurea, N'-para-chlorophenyl-O,N,N-trimethylisourea, N'-p-chlorophenyl-N-methoxy-N-methylurea, N,N-dimethyl-N'-phenylurea, 3-(4-bromophenyl)-1-methoxy-1-methylurea, 1-(2-benzothiazolyl)-3-methylurea, N,N-dimethyl-N'-(4-[1-methylethyl]phenyl)urea, N'-(3,4-dichlorophenyl)-N-methoxy-N-methylurea or N,N-dimethyl-N'-[3-(trifluoromethyl)phenyl]urea.

The triazine herbicide generally comprises 2-chloro-4-(1-cyano-1-methylamino)-6-ethylamino-1,3,5-triazine or 2-isopropylamino-4-(3-methoxypropylamino)-6-methylthio-1,3,5-triazine or a compound of the formula:

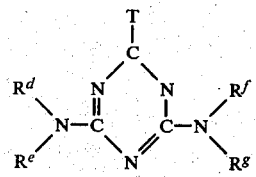

where T is a halogen atom, OY group or SY group, where Y is an alkyl group, $R^d$ and $R^f$ are the same or different and are hydrogen or alkyl and $R^e$ and $R^g$ are the same or different alkyl groups, such as 2-chloro-4,6-bisethylamino-1,3,5-triazine, 2-chloro-4-ethylamino-6-diethylamino-1,3,5-triazine, 2-chloro-6-ethylamino-4-isopropylamino-1,3,5-triazine or 2,4-bis(isopropylamino)-6-methylthio-1,3,5-triazine.

The phenol herbicide generally comprises 4,6-dinitro-o-cresol, 4,6-dinitro-2-sec-butylphenol or pentachlorophenol. The nitrile herbicide generally comprises 3,5-diiodo-4-hydroxy-benzonitrile, 3,5-dibromo-4-hydroxybenzonitrile or 2,6-dichlorobenzonitrile. The bipyridylium herbicide generally comprises 1,1'-dimethyl-4,4'-bipyridylium dichloride or 1,1'-ethylene-2,2'-bipyridylium dibromide. The substituted benzoic acid herbicide generally comprises 2,3,6-trichlorobenzoic acid, 2-methoxy-3,6-dichlorobenzoic acid or N-(1,1-dimethylpropynyl)-3,5-dichlorobenzamide. The halogenated aliphatic acid herbicide generally comprises trichloroacetic acid or 2,2-dichloropropionic acid. The carbamate herbicide generally comprises isopropyl N-(3-chlorophenyl) carbamate, 4-chloro-2-butynyl N-(3-chlorophenyl)carbamate, methyl 3-(m-tolylcarbamoyloxy)phenylcarbamate or D-N-ethyl-2-(phenylcarbamoyloxy)propionamide. The thiocarbamate herbicide generally comprises S-ethyl N,N-dipropylthiocarbamate, S-ethyl N,N-diisobutylthiocarbamate, S-(2,3-dichloroallyl) N,N-diisopropylthiocarbamate, S-ethyl N-ethyl-N-cyclohexylthiocarbamate, S-propyl butylethylthiocarbamate or S-(2,3,3-trichloroallyl) N,N-diisopropylthiocarbamate. The chloroacetamide herbicide generally comprises N,N-diallyl-2-chloroacetamide or N-isopropyl-2-chloroacetanilide. The diazine herbicide generally comprises 5-bromo-6-methyl-3-sec-butyluracil, 3-cyclohexyl-5,6-trimethyleneuracil, 5-amino-4-chloro-2-phenyl-3-pyridazinone or 1,2-dihydropyridazine-3,6-dione. The arsenic herbicide generally comprises a salt of methane arsonic acid or cacodylic acid. Other herbicides which may be used include 1,2-dimethyl-3,5-diphenylpyrazolium ion, ethyl N-benzoyl-N-(3,4-dichlorophenyl)alanine, N-isobutyl-2-oxo-1-imidazolidine-carboxamide, aminotriazole, 2,3-dichloro-1,4-naphthoquinone, 4-amino-3,5,6-trichloropicolinic acid, N,N-dimethyl-2,2-diphenylacetamide, 2,6-dinitro-N,N-dipropyl-4-trifluoromethylaniline, N-butyl-N-ethyl-2,6-dinitro-4-trifluoromethylaniline, S,S,S-tributyl phosphorotrithioate, 2-ethoxy-2,3-dihydro-3,3-dimethyl-5-benzofuranyl methylsulphonate, 4-chloro-2-oxobenzothiazolin-3-yl acetic acid, 3-isopropyl-2,1,3-benzothiadiazinon-(4)-2,2-dioxide, 3,5-dibromo-4-hydroxybenzaldehyde, 2,4-dinitrophenyloxime, methyl 2-chloro-3-(4-chlorophenyl)-propionate, 2-chloroethyltrimethylammonium chloride, 4-methylsulphonyloxy-2-butynyl m-chlorocarbanilate, isopropyl 2-(N-benzoyl-3-chloro-4-fluoroanilino)propionate, methyl 2-(N-benzoyl-3-chloro-4-fluoroanilino)-propionate, b 2-chloro-N-(1,3-dioxolan-2-ylmethyl)-2',6'-dimethylacetanilide or 2-chloro-1-(3-ethoxy-4-nitrophenoxy)-4-trifluoromethylbenzene.

The compounds may also be employed in association with a herbicidal antidote (a substance having the property of improving the safety of a herbicide to a crop), e.g. N,N-diallyl-2,2-dichloroacetamide, 4'-chloro-2-(hydroxyimino)acetanilide, 1,8-naphthalic anhydride, α-(cyanomethoxyimino)-benzeneacetonitrile or 2,2-dimethyl-3-dichloroacetyloxazolidine. Although the antidote may be applied in admixture with active compound, it is preferably applied separately, and especially as a treatment for crop seeds. The ratio by weight of herbicide to antidote is preferably from 1:4 to 4:1.

The present compounds may be used in admixture or sequence with a fungicide, for instance one or more of maneb (polymeric manganese ethylenebisdithiocarbamate), zineb (zinc ethylenebisdithiocarbamate), mancozeb (which can be regarded as a mixture of maneb and zineb), thiram (tetramethylthiuram disulphide), ditalimfos (O,O-diethyl phthalimidophosphonothioate), tridemorph (2,6-dimethyl-4-tridecylmorpholine), fluotrimazole (1-[diphenyl-(3-trifluoromethylphenyl)methyl]-1,2,4-triazole), ethirimol (5-butyl-2-ethylamino-4-hydroxy-6-methylpyrimidine), triforine (1,4-di[2,2,2-trichloro-1-formamidoethyl]piperazine), pyracarbolid (3,4-dihydro-6-methylpyran-5-carboxanilide), zinebethylene thiuramdisulphide adduct, carbendazim (methyl benzimidazol-2-ylcarbamate), captafol (3a,4,7,7a-tetrahydro-N-[1,1,2,2-tetrachloroethyanesulphenyl]-phthalimide), thiophanate (1,2-di[3-ethoxycarbonyl-2-thioureido]benzene), proprineb (polymeric zinc propylenebisdithiocarbamate) oxycarboxin (2,3-dihydro-6-methyl-5-phenylcarbamoyl-1,4-oxathiin 4,4-dioxide), quintozene (pentachloronitrobenzene), benomyl (methyl 1-[butylcarbamoyl]benzimidazol-2-ylcarbamate) and benadanil(2-iodobenzanilide).

The present compounds may be used in admixture or sequence with an insecticide. The insecticide may be for instance one or more of demeton-S-methyl (S-2-ethylthioethyl O,O-dimethyl phosphorothioate), dimethoate (O,O-dimethyl S-methylcarbamoylmethyl phosphorodithioate), formothion (S-[N-formyl-N-methylcarbamoylmethyl] O,O-dimethyl phosphorodithioate), oxydemeton-methyl (S-2-ethylsulphinylethyl O,O-dimethyl phosphorothioate), pirimicarb (2-dimethylamino-5,6-dimethylpyrimidin-4-yl dimethylcarbamate,), thiometon (S-2-ethylthioethyl O,O-dimethyl phosphorodithioate), BHC (benzene hexachloride), aldrin (1,2,3,4,10,10-hexachloro-1,4a,4,5,8,8a-hexahydro-exo-1,4-endo-5,8-dimethanonaphthalene), fenitrothion (O,O-dimethyl O-4-nitro-m-tolyl phosphorothioate), omethoate (O,O-dimethyl S-methylcarbamoylmethyl phosphorothioate), pirimiphos-methyl (O-2-diethylamino-6-methylpyrimidin-4-yl O,O-dimethyl phosphorothioate) and DDT (1,1,1-trichloro-2,2-di[chlorophenyl]ethane).

The ratio of the present compound to the second herbicide may vary over a wide range according to the particular compounds involved and the intended use. In general the ratio of present compound to second herbicide lies in the range 1:0.1 to 1:15.

The present compounds are usually employed for herbicidal purposes at a rate of from 0.5 to 8 kg per hectare, for example, 1 to 4 kg per hectare.

The present compounds may be applied to plants, the soil, land or aquatic areas.

The present compounds may be in admixture with non-phytotoxic oils, e.g. Agri-Oil Plus, Sun Oil 11E or Fyzol E.

The compounds may be in admixture with fertilizers.

As mentioned above, the present invention provides a method of controlling or preventing fungal growth which comprises applying to a locus infested or liable to be infested by fungus a compound or composition according to the invention.

The locus infected or liable to be infected may be plants, animals, the soil, aquatic areas, fabrics, textiles, paper, wood and the like.

Preferably the compound or composition is employed against fungal diseases of plants. The plants may be growing or may be seeds, using 'seeds' in the wider sense to include tubers etc. The compound or composition can be applied directly to the plants, or can be applied to the medium in which they grow and be taken up by the plants and distributed within the plants, i.e. the compounds show systemic activity.

The compounds are applied to a locus infested or liable to be infested with fungus at a rate for example of 0.2 to 5 kg per hectare. For use as a seed dressing, the compounds may be applied in the form of a dust with a solid carrier for instance at the rate of 1-4 e.g. 2 oz of dust per bushel of seed or may be applied in the form of a liquid with a liquid carrier for instance at a rate of 0.75-3 fluid oz of liquid per bushel of seed.

For fungicidal purposes we prefer to use compounds of formula I in which $R^1$ is —$CH_2CH_2COOH$ or a salt or ester thereof.

The compounds of formula I may in certain instances exist in tautomeric or isomeric forms.

The invention is further described, though only by way of illustration, in the following Examples.

EXAMPLE 1

Monosodium Monomethyl Acetylphosphonate

Dimethyl acetylphosphonate (10 g, 0.066 mol) and sodium iodide (15 g, 0.1 mol) were dissolved in acetone (80 ml) and the solution was stirred and refluxed for 6 hours. After cooling, the precipitated solid was filtered off, washed with acetone and ether and then air dried. Yield=9.5 g, m.p. decomp >170°. The NMR spectrum was consistent with the proposed structure.

| Analysis | C | H |
|---|---|---|
| $C_3H_6NaO_4P$ requires: | 22.51 | 3.78 |
| Found: | 23.00 | 4.09 |

EXAMPLE 2

Monosodium monomethyl (1-oxopropyl)phosphonate

Dimethyl (1-oxopropyl)phosphonate (10.0 g, 0.060 mol) and sodium iodide (9.0 g, 0.060 mol) were dissolved in ethyl methyl ketone (160 ml) and the solution stirred and refluxed for 16 hours.

After cooling, the solvent was decanted from the wet looking sodio salt, and the latter evaporated to dryness in vacuo. The NMR spectrum was consistent with the proposed structure m.p. 73°–74° C.

| Analysis | C | H |
|---|---|---|
| $C_4H_8NaO_4P$ requires: | 27.60 | 4.36 |
| Found: | 27.21 | 4.70 |

EXAMPLE 3

Monosodium monomethyl benzoylphosphonate

Dimethyl benzoylphosphonate (12.8 g, 0.06 mol) and sodium iodide (9.0 g, 0.06 mol) were dissolved in ethyl methyl ketone (160 ml) and the solution stirred and refluxed for 16 hours. There was evidence of a precipitation after about 10 minutes refluxing.

After cooling, the sodio salt was filtered off, washed with fresh ethyl methyl ketone, then ether and finally dried in vacuo over $CaCl_2$. Yield=12.8 g, m.p. 256°–7° C. The NMR spectrum was in agreement with the proposed structure.

| Analysis | C | H |
|---|---|---|
| $C_8H_8O_4NaP$ requires: | 43.26 | 3.63 |
| Found: | 42.97 | 3.97 |

EXAMPLE 4

Monosodium monomethyl (1-oxobutyl)phosphonate

Dimethyl (1-oxobutyl)phosphonate (10.8 g, 0.06 mol) and sodium iodide (9.0 g, 0.06 mol) were dissolved in ethyl methyl ketone (160 ml) and the solution stirred and refluxed for 16 hours.

There was no precipitation until the solution was cooled. The sodio salt was filtered off, washed with fresh ethyl methyl ketone, then ether and finally dried in vacuo over $CaCl_2$. Yield=9.8 g, m.p. 70°–1° C. The NMR spectrum was in agreement with proposed structure.

| Analysis | C | H |
|---|---|---|
| $C_5H_{10}O_4NaP$ requires: | 31.93 | 5.36 |
| Found: | 31.45 | 5.74 |

EXAMPLE 5

Monosodium monomethyl (2-methyl-1-oxopropyl)phosphonate

Dimethyl (2-methyl-1-oxopropyl)phosphonate (10.8 g, 0.06 mol) and sodium iodide (9.0 g, 0.06 mol) were dissolved in ethyl methyl ketone (160 ml) and the solution stirred and refluxed for 16 hours. There was evidence of a precipitate after about 10 minutes refluxing.

After cooling the sodio salt was filtered off, washed with ethyl methyl ketone, then ether and finally dried in vacuo over $CaCl_2$. Yield=10.9 g, m.p. 198°–200° C. The NMR spectrum was consistent with the proposed structure.

| Analysis | C | H |
|---|---|---|
| $C_5H_{10}O_4NaP$ requires: | 31.93 | 5.36 |
| Found: | 31.49 | 5.69 |

EXAMPLE 6

Monosodium acetylphosphonate

The product compound of Example 1 (4.5 g, 0.028 mol) was dissolved in the minimum amount of water (~17 ml) and passed down a cation exchange column (H+ form, equilibrated with water). Elution with water was continued until the eluent was no longer strongly acid (~38 ml). The eluent was freeze dried to give a yellow oil.

The oil was then taken up in ethyl methyl ketone (70 ml), sodium iodide (4.2 g, 0.028 mol) added and the solution stirred and refluxed. Evidence of precipitation was seen after about 5 minutes, and after 2 hours it was judged to be about quantitative. Hence the reaction was terminated.

After cooling the precipitate was filtered off, washed with fresh ethyl methyl ketone, then ether and finally the pale yellow solid was dried in vacuo over $CaCl_2$. Yield=3.3 g, m.p. 188°–90° C. The IR and NMR spectra were consistent with the proposed structure.

| Analysis | C | H |
|---|---|---|
| $C_2H_4O_4PNa$ requires: | 16.45 | 2.76 |
| Found: | 16.02 | 3.08 |

EXAMPLE 7

Monosodium monoethyl acetylphosphonate

A solution of diethyl acetylphosphonate (5 g, 0.028 mol) and oven-dried sodium iodide (4.2 g, 0.028 mol) in molecular sieve dried ethyl methyl ketone (75 ml) was stirred and refluxed for 16 hours.

After cooling, the deliquescent precipitate was filtered off, washed with ethyl methyl ketone and dried in vacuo over $CaCl_2$. The IR and NMR spectra were consistent with the proposed structure. Yield=3.2 g, m.p. decomp above 90°.

| Analysis | C | H |
|---|---|---|
| $C_4H_8O_4PNa$ requires: | 27.60 | 4.63 |
| Found: | 27.25 | 4.57 |

EXAMPLE 8

Sodium acetylmethylphosphinate (a) The ketal of Example 17 (44 g) was dissolved in acetic acid (250 ml), containing 3% added water, with warming on a steam bath. The dark red solution was allowed to stand for 16 hours. Acetic acid was removed in vacuo, as much of the residual acid as possible was removed with benzene (3×100 ml) and the resulting red oil was dissolved in acetone. The required product crystallised on cooling and was filtered off and well washed with acetone. The filtrate was evaporated in vacuo and the above procedure was successively repeated until no more of the product was obtained. The combined yield of these fractions, which were identical by IR and NMR spectra, was 22.0 g m.p. (d) 186°–188° C.

| Analysis | | |
|---|---|---|
| Found: | C 24.91 | H 4.56 |
| $C_3H_6NaO_3P$ Requires: | C 25.01 | H 4.20 |

(b) A solution of methyl acetylmethylphosphinate (1.5 g, approx 0.01 mol) and oven-dried sodium iodide (1.5 g, 0.01 mol) in molecular sieve dried ethyl methyl ketone (70 ml) was stirred and refluxed for 1 hour. The yellow precipitate was isolated by decanting and dried in vacuo over anhydrous $CaCl_2$.

The NMR spectrum showed this to be the required material. Yield=1.3 g.

EXAMPLE 9

Methyl 4-(hydroxymethoxyphosphinyl)-4-oxobutanoate sodium salt

A solution of methyl 4-(dimethoxyphosphinyl)-4-oxobutanoate (22.4 g, 0.1 mol) and oven-dried sodium iodide (15.0 g, 0.1 mol) in molecular sieve dried ethyl methyl ketone (200 ml) was stirred and refluxed for 16 hours.

On cooling a yellow glass-like solid was precipitated. This was filtered off and dried in vacuo over anhydrous $CaCl_2$. (The product was very deliquescent). Yield=22.6 g. (Theory=23.2 g) m.p. 56°–8°.

The IR and NMR spectra were consistent with the desired structure.

| Analysis | C | H |
|---|---|---|
| $C_6H_{10}O_6PNa$ requires: | 31.05 | 4.34 |
| Found: | 30.83 | 4.77 |

EXAMPLE 10

Methyl 4-oxo-4-phosphonobutanoate monosodium salt

A solution of the product of Example 9 (5.0 g, 0.0215 mol) in formic acid (50 ml) was refluxed for 2½ hours. The solution was evaporated in vacuo. Toluene (~25 ml) was added to the residue and was evaporated to dryness. This procedure was repeated twice. The NMR spectrum was consistent with the proposed structure.

The residue was purified by dissolving it in a small volume of formic acid and diluting carefully with acetone. The precipitated solid was filtered off, washed with acetone and then with ether and dried in vacuo over anhydrous $CaCl_2$. Yield=1.3 g, m.p. decomp >190° C.

| Analysis | C | H |
|---|---|---|
| $C_5H_8O_6PNa$ requires: | 27.54 | 3.70 |
| Found: | 27.10 | 3.55 |

EXAMPLE 11

Sodium acetylphenylphosphinate

Methyl acetylphenylphosphinate (5.0 g, 0.025 mol) was added to a solution of sodium iodide (3.8 g, 0.025 mol) in molecular sieve dried ethyl methyl ketone (50 ml) and the resulting solution was stirred and refluxed for 15 minutes.

The resulting precipitate was filtered off, washed with ethyl methyl ketone and then thoroughly with ether and dried in vacuo over anhydrous CaCl$_2$.

The NMR spectrum indicated that the required material had been formed.

The product was recrystallised twice from methanol/acetone (approximately 1:2).

Yield = 1.2 g. m.p. >300°

| Analysis | C | H |
|---|---|---|
| C$_8$H$_8$O$_3$PNa requires: | 46.62 | 3.91 |
| Found: | 46.83 | 4.03 |

EXAMPLE 12

Sodium (1-oxopropyl)pentylphosphinate

Methyl (1-oxopropyl)pentylphosphinate (6.2 g) and sodium iodide (4.5 g) were refluxed for 1 hour in methyl ethyl ketone (50 ml). The resulting solution was cooled and evaporated in vacuo to give the crude sodium salt as a very deliquescent pale yellow solid (6.3 g). The NMR spectrum confirmed production of the title compound.

EXAMPLE 13

Methyl 4-(hydroxypentylphosphinyl)-4-oxobutanoate sodium salt

Methyl 4-(methoxypentylphosphinyl)-4-oxobutanoate (7.9 g) was reacted with sodium iodide (4.5 g) in methyl ethyl ketone (80 ml) in the same manner as in Example 12. The product, obtained on evaporation, was a pale yellow very deliquescent solid (8.1 g). NMR consistent with the required structure.

| Analysis | C | H |
|---|---|---|
| C$_{10}$H$_{18}$NaO$_5$P requires: | 44.12 | 6.67 |
| Found: | 43.69 | 6.82 |

EXAMPLE 14

Sodium acetylpentylphosphinate

A solution of methyl acetylpentylphosphinate (5.0 g, 0.026 mol) and oven-dried sodium iodide (3.9 g, 0.026 mol) in freshly distilled ethyl methyl ketone (50 ml) was refluxed for 1hour.

The solvent was evaporated in vacuo and the yellow deliquescent solid was dried in vacuo over CaCl$_2$.

Yield = 5.0 g m.p. 88°–90°.

The IR and NMR spectra were consistent with the desired structure.

EXAMPLE 15

Sodium acetylethylphosphinate

Methyl acetylethylphosphinate (6 g)was reacted with sodium iodide (6.0 g) in ethyl methyl ketone (50 ml) in the same manner as in Example 12. The solution was stirred and refluxed 1.25 hours, cooled and the product filtered off and washed with a little ethyl methyl ketone and dried in vacuo (5.3 g). Decomposes 192°–4°.

| Analysis | C | H |
|---|---|---|
| C$_4$H$_8$NaO$_3$P requires: | 30.39 | 5.10 |
| Found: | 29.99 | 5.35 |

EXAMPLE 16

Methyl (1,1-dimethoxyethyl)methylphosphinate

Methyl phosphonous dichloride (90 g) was added dropwise, with magnetic stirring and cooling to trimethyl ortho-acetate (210.0 g) under nitrogen. The temperature of the reaction was kept at −20° to −25° C. The mixture was allowed to warm up overnight, residual orthoacetate was removed at 20 mm/Hg and the residue distilled to give, after a very small forerun the desired ketal b.p. 90°–92°/2.5 mm/Hg (123.3 g = 88%). The NMR spectrum was consistent with the required structure.

| Analysis | | |
|---|---|---|
| Found: | C 40.00% | H 8.32% |
| C$_6$H$_{15}$O$_4$P Requires: | C 39.56% | H 8.30% |

EXAMPLE 17

Sodium (1,1-dimethoxethyl)methylphosphinate

The ester product of Example 16 (63.7 g) was refluxed for 2 hours under nitrogen with stirring, in ethyl methyl ketone (400 ml) containing sodium iodide (57.5 g). After 2 hours the reaction product crystallised and the mixture became impossible to stir. The product was filtered off and washed with acetone and crystallised from methanol/acetone as colourless needles (49.1 g) (Yield from three successive crops). Decomposes 255°–7°. IR and NMR consistent with the desired product.

A sample of the sodium salt was recrystallised from methanol/acetone to give colourless needles m.p. (d) 262°–265°.

| Analysis | | |
|---|---|---|
| Found: | C 31.86% | H 6.47 |
| C$_5$H$_{12}$NaO$_4$P Requires: | C 31.59% | H 6.36 |

EXAMPLE 18

Sodium (1,1-dimethoxyethyl)methylphosphinate

The phosphinate ester product of Example 16 (220 g) was refluxed 2 hr with aqueous sodium hydroxide (2 N: 660 ml). The cooled solution was taken to pH 7.0 with conc. hydrochloric acid, evaporated in vacuo and the solid residue was triturated with methanol and insoluble material filtered off. The filtrate was again evaporated to dryness, the residue triturated with methanol and further insoluble material filtered off. The filtrate was finally evaporated to dryness, triturated with acetone and filtered to give the title compound (2.9 g) mp 258°–262° C., identical (ir nmr) with the product from Example 17.

EXAMPLE 19

Methyl -b 4-(hydroxymethylphosphinyl)-4-oxobutanoate lithium salt

(a) Methyl 4-(methoxymethylphosphinyl)-4-oxobutanoate

A solution of dimethyl methylphosphonite (27.3 g) in benzene (300 ml) was added with stirring to a solution of methyl 4-chloro-4-oxobutanoate (37.9 g) in benzene (200 ml). The temperature was kept at 25°–30° C. After 16 hours the solvent was evaporated off under reduced pressure and the residue distilled to give the sub-title product, boiling point 126° C./0.2 mmHg.

(b) Methyl 4-(hydroxymethylphosphinyl)-4-oxobutanoate lithium salt

The product of step (a) (16.0 g) was dissolved in a 0.5 M solution of anhydrous lithium iodide in methyl isobutyl ketone (170 ml) and the solution heated under reflux with stirring for 2 hours. After cooling the crude lithium salt was filtered off, washed with acetone and dried. The product (12.0 g) was dissolved in methanol (50 ml) and diluted with acetone (500 ml). The precipitated impurities were filtered off and the filtrate was evaporated to dryness to give the title product as a deliquescent, pale yellow solid (9.5 g). The salt has no sharp melting point and gradually softens and decomposes above 195° C. Elemental analysis indicates the monohydrate:

| Analysis | C | H |
|---|---|---|
| $C_6H_{10}LiO_5P \cdot H_2O$ requires: | 33.05 | 5.55 |
| found: | 33.07 | 5.57% |

EXAMPLE 20

4-(Hydroxymethylphosphinyl)-4-oxobutanoic acid dilithium salt

A solution of the product of Example 20 (7.0 g) in dimethylformamide (30 ml) was added to a 0.5 M solution of anhydrous lithium iodide in methyl isobutyl ketone (155 ml). The mixture was heated under reflux with stirring for 6 hours and filtered off to give the crude dilithium salt which was washed with acetone and dried. The crude salt was dissolved in methanol (30 ml), the solution was diluted with acetone (250 ml) and the reprecipitated salt was filtered off, washed with acetone and oven-dried. Yield 5.5 g.

| Analysis | C | H |
|---|---|---|
| $C_5H_7Li_2O_5P$ requires: | 31.28 | 3.68% |
| found: | 31.23 | 4.06% |

EXAMPLE 21

Sodium methyl(2-methyl-1,3-dioxolan-2-yl)phosphinate

(a) Ethyl methyl(2-methyl-1,3-dioxolan-2-yl)phosphinate

This was prepared from 2-ethoxy-2-methyl-1,3-dioxolane (31.0 g) and methyl phosphonous dichloride (11.0 g). The product distilled at 137°–138° at 27 mmHg.

Yield=13.0 g (71). The i.r. and n.m.r spectra were in agreement with the required structure.

| Analysis | | |
|---|---|---|
| $C_7H_{15}O_4P$ requires: | C: 43.30; | H: 7.79% |
| found: | C: 43.68; | H: 7.76% |

(b) Sodium methyl(2-methyl-1,3-dioxolan-2-yl)phosphinate

Th product of step (a) (7.7 g) was refluxed for 2 hours with 1 N sodium hydroxide solution (40 ml). The cooled solution was evaporated in vacuo, traces of water were removed with ethanol and the residue triturated with ethanol to give the required sodium salt (7.2 g) softens 220° C., darkens but does not melt below 300° C.

| Analysis | | |
|---|---|---|
| $C_5H_{10}NaO_4P$ requires: | C 31.93; | H 5.36% |
| found: | C 31.83; | H 5.32% |

EXAMPLE 22

Sodium (2-methyl-1,3-thiazolidin-2-yl)phosphonite

2-Mercaptoethylamine hydrochloride (2.3 g, 0.02 mol) was stirred in ethanol (20 ml) with sodium hydroxide (0.8 g, 0.02 mol) for about 40 min, and the cloudy solution then filtered. This solution was added to sodium acetylphosphonite (2.6 g, 0.02 mol) stirred in a further 20 ml of ethanol. Stirring was continued overnight, and the mixture then evaporated under reduced pressure giving a slightly gummy white solid. Evaporation from an ethanol-ether mixture gave a fine powder. (3.1 g). This material was ground up in ethanol and filtered giving a solid residue. The filtrate was treated with ether when a gummy solid precipitated. The mixture was filtered and the gummy solid residue was ground up in dry ether and collected by filtration. The solid residues were combined, taken up in ethanol, re-evaporated and dried under vacuum giving a cream solid (1.2 g, 32%), M.P. (decomp) 310°. N.m.r indicated this was the desired product.

| Analysis | C | H | N |
|---|---|---|---|
| $C_4H_8NNaO_2PS \cdot H_2O$ requires: | 22.30 | 4.89 | 6.79 |
| Found: | 22.84 | 5.04 | 6.28 |

EXAMPLE 23

Sodium (2-methylperhydro-1,3-diazin-2-yl)phosphonite

Sodium acetylphosphinate (2.6 g, 0.02 mol) and 1,3-diaminopropane (1.7 ml, 1.5 g, 0.02 mol) were stirred together in ethanol (60 ml) for 2½ days, giving a cloudy pale yellow solution. This was evaporated inder reduced pressure, giving a sticky hydroscopic yellow solid, which contains ethanol by nmr. The solid was dissolved in ethanol, toluene added and re-evaporated to dryness, giving a yellow foam, mp 144°–6°, decomp (3.2 g, 86%). NMR was consistent with the desired structure.

| Analysis: | C | H | N |
|---|---|---|---|
| $C_5H_{12}N_2NaO_2P$ requires: | 32.26 | 6.50 | 15.05 |

| Analysis: | C | H | N |
|---|---|---|---|
| Found: | 27.9 | 6.1 | 12.25 |

EXAMPLE 24

Sodium acetylphosphonite

The diethyl ketal of sodium acetylphosphonite (9.8 g) was dissolved in a mixture of acetic acid (95 ml) and water (5 ml) and the solution was kept at ambient temperature for 16 hours. The solvent was removed in vacuo and the residue was triturated with acetone to give the crude product. (6.3 g). A small sample was dissolved in cold methanol and diluted with acetone. The required ketone crystallised on storage; mp>340° C.

| Analysis: | C | H |
|---|---|---|
| $C_2H_4NaO_3P$ requires: | 18.48 | 3.1 |
| Found: | 18.38 | 3.25 |

Recrystallisation on a large scale led to partial conversion of the ketone to the dimethyl ketal. The ketone then had to be regenerated as above to give the required material (18. g) identical with the above.

EXAMPLE 25

Sodium (1,1-diethoxyethyl)phosphonite

Hypophosphorous acid (30% w/v) (22 ml, 0.1 mol) was evaporated at 0.5 mm Hg at 50° to remove the water. Triethyl orthoacetate (40.5 g, 0.25 mol) was added to the anhydrous acid under $N_2$, and dry HCl gas was passed into the stirred mixture until it turned cloudy (approx. 10 sec). The resulting mixture was stirred at room temperature under $N_2$ for 16 h.

The resulting mixture was evacuated at 0.1 mm Hg for 1 h at room temperature to remove all volatile material.

A solution of sodium hydroxide (6 g, 0.15 mol) in water (60 ml) (deoxygenated with $N_2$) was added to the residue and the resulting solution was refluxed under $N_2$ for 2 h.

After cooling, the solution was neutralised to pH 8 with conc. HCl and the solution was evaporated to dryness. The residue was dissolved in boiling ethanol (125 ml), filtered and the filtrate evaporated to dryness in vacuo.

Recrystallisation of the residue from ethanol afforded the title compound, yield=3.0 g, mp 165°-8° (dec). The i.r and n.m.r spectra were in agreement with the proposed structure.

| Analysis | C | H |
|---|---|---|
| $C_6H_{14}NaO_4P$ requires: | 35.3 | 6.91 |
| Found: | 34.9 | 6.79 |

EXAMPLE 26

Sodium (1,1-diethoxyethyl)methylphosphinate

The corresponding ethyl ester was made as in Example 16 using triethyl ortho-acetate and methylphosphonous dichloride. It boiled at 126°-9° C. at 23 mm Hg.

This ester (7.5 g) was refluxed with aqueous 1 N sodium hydroxide (50 ml) until a solution was obtained (1 hour), and then for a further hour. The cooled solution was evaporated in vacuo and the residual water removed with ethanol. The residue was triturated with acetone to give a solid (4.0 g). This product was crystallised from ethanol/acetone to give the required sodium salt (1.7 g) softens 155°, mp 198°-201° C. (dec).

| Analysis: | C | H |
|---|---|---|
| $C_7H_{16}NaO_4P$ requires: | 38.54 | 7.39 |
| Found: | 38.16 | 7.04 |

EXAMPLE 27

Sodium methyl(2-methyloxathiolan-2-yl)phosphinate

2-Ethoxy-2-methyloxathiolane (24 g, 0.16 mol) was stirred under a slow stream of nitrogen with a spatula end of $SnCl_2$. Methane phosphonous dichloride (7.5 g, 0.065 mol), was added dropwise, the mixture being cooled to about $-5°$ C. with a dry-ice/acetone bath during the addition. The reaction was stirred overnight. The mixture was then distilled under reduced pressure, the main fraction collected distillled at 162°-167° at 30 mm Hg, leaving a black residue. The n.m.r was consistent with ethyl methyl(2-methyloxathiolan-2-yl)phosphinate.

This material (0.44 mol) and 1 N NaOH (44 ml, 0.044 mol) were heated together under reflux for 5 h, then allowed to stand overnight. The solution was filtered and evaporated to give a pale yellow solid which was recrystallised from ethanol/ether giving 3.6 g (41%) of product, n.m. r consistent with desired product. M.P. (decomp) 310° after some charring at 285°.

| Analysis: | C | H |
|---|---|---|
| $C_5H_{10}NaO_3PS$ requires: | 29.41 | 4.94 |
| Found: | 28.94 | 5.01 |

EXAMPLE 28

Sodium methyl(2,4,5-trimethyl-1,3-dioxolan-2-yl)phosphinate

2-Ethoxy-2,4,5-trimethyl-1,3-dioxolane (28 g, 0.175 mol) was stirred under a slow stream of nitrogen with a spatula end of $SnCl_2$. Methanephosphonous dichloride (8.2 g, 0.07 mol) was added dropwise, cooling the reaction in a dry ice/acetone bath as necessary to control the exothermic reaction. When addition was complete the mixture was left to stir for 2½ days. The mixture was distilled under high vacuum, the fraction boiling 64°-75° (pressure rising from 0.15 to 0.45 mm Hg) contained the desired product, ethyl methyl(2,4,5-trimethyl-1,3-dioxolan-2-yl)phosphinate, 16.9 g 95%.

The above ethyl ester (8 g, 0.036 mol) was heated at reflux in 1 N NaOH (36 ml, 0.036 mol) for 2 h, and then allowed to stand overnight at room temperature. The solution was evaporated under reduced pressure giving a white solid which was dried in vacuo. 7.2 g, 92% obtained. The n.m.r was consistent with the desired product.

M.P. (decomp)≃250° C.

| Analysis: | C | H |
|---|---|---|
| $C_7H_{14}NaO_4P$ requires: | 41.9 | 6.2 |

| Analysis: | C | H |
|---|---|---|
| Found: | 39.2 | 6.75 |

EXAMPLE 29

Sodium methyl(1,1-dipropoxyethyl)phosphiante

Methane phosphonous dichloride (5.7 ml, 0.063 mol) was added dropwise at 0° to tripropyl orthoacetate (32.1 g, 0.157 mol) stirred under nitrogen with a little $SnCl_2$. When the addition was complete the mixture was allowed to warm to room temperature and was stirred overnight. The mixture was distilled under high vacuum to give propyl methyl(1,1-dipropoxyethyl)phospinate b p 95°–100° at 0.3 mm Hg, 14.3 g, 85%. This product (14.3 g, 0.054 mol) was refluxed in 1 N NaOH solution (90 ml, 0.08 mol) and ethanol added until the reaction mixture was homogeneous (approx 100 ml added). The solution was refluxed for 24 h, then cooled and evaporated. The residue was taken up in water and neutralised to pH 4.6 with dil. HCl, evaporated three times from water to remove excess HCl and then taken up in ether and filtered to remove any NaCl. This was repeated 2 or 3 times until there was no inorganic material in the solution, which was evaporated to give a yellow oil which solidified slowly. N.m.r indicated the presence of a little sodium acetyl methyl phosphinate in addition to the desired product.

| Analysis: | C | H |
|---|---|---|
| $C_9H_{20}NaO_4P$ requires: | 43.9 | 8.19 |
| Found: | 42.17 | 8.37 |

EXAMPLE 30

Sodium (1-methoxyvinyl)methylphosphinate (a) Methyl (1-methoxyvinyl)methylphosphinate A solution of methyl (1,1-dimethoxyethyl)methanephosphinate (8 g) in dry xylene (40 ml) containing concentrated $H_2SO_4$ (8 drops) was refluxed for 4 days.

The solvent was evaporated in vacuo. Distillation in vacuo afforded (after a small fore-run) a fraction bp 45°–50° at 0.1 mm Hg. Yield = 1.8 g.

An n.m.r. spectrum showed that this product was the required compound.

(b) Sodium (1-methoxyvinyl)methylphosphinate

A solution of the product of step (a) (0.43 g, 2.87 mmol) and oven dried sodium iodide (0.43 g, 2.87 mol) in distilled ethyl methyl ketone (6 ml) was stirred and refluxed for 16 h.

The resulting precipitate was filtered off, washed with fresh ethyl methyl ketone and then ether and dried in vacuo over $CaCl_2$.

The n.m.r and i.r spectra were consistent with the proposed structure.

Recrystallisation from ethanol/ether gave the pure compound mp, decomp. above 240° (softening at 230°).

| Analysis: | C | H |
|---|---|---|
| $C_4H_8NaO_3P$ requires: | 30.39 | 5.1 |
| Found: | 29.9 | 5.42 |

EXAMPLE 31

Sodium (1-ethylthiovinyl)methylphosphinate

Methyl acetylmethylphosphinate (5.4 g, 0.04 mol) and ethanethiol (9.9 g, 11.7 ml, 0.16 mol) were stirred together in chloroform (40 ml) at room temperature under nitrogen. Trimethylsilyl chloride (6.5 g, 7.6 ml, 0.06 mol) was added dropwise over 10 min and the mixture then stirred for a further 1 hour. The solution was washed with 2.5 M NaOH (3×50 ml) and with brine, then dried and evaporated giving a yellow liquid, 5.5 g. N.m.r showed this to consist mainly of a mixture of the bisthioketal and vinylsulphide derivatives of the starting ester. A portion of this material (2.7 g≃0.015 mol) was heated with sodium iodide (2.3 g, 0.015 mol) in methyl isobutyl ketone (20 ml) under reflux in a nitrogen atmosphere for 1½ h. By the end of this time a considerable precipitate had formed. This was collected by filtration. Some more material precipitated from the liquor on standing and was also collected. The combined precipitates were washed with a little ethyl methyl ketone and dried in vacuo, giving 1.8 g product, 64%. N.m.r was consistent with the desired product.

EXAMPLE 32

Sodium methyl(2-methylperhydro-1,3-diazin-2-yl)phosphinate

Sodium acetylmethylphosphinate (2.9 g, 0.02 mol) and 1,3-diaminopropane (1.7 ml, 1.5 g, 0.02 mol) were stirred together in ethanol (60 ml) for 2½ days and then evaporated under reduced pressure. The white solid was dried in vacuo, removing most of the ethanol. No unreacted starting material remained by N.m.r. The purity was estimated as approximately 95% from n.m.r, 4.1 g product was obtained.

EXAMPLE 33

Sodium methyl(2-methylperhydro-1,3-thiazin-2-yl)phosphinate

3-Mercaptopropylamine hydrochloride (2.6 g, 0.02 mol) was stirred in ethanol (25 ml) with sodium hydroxide (0.8 g, 0.02 mol) for about 1½ hours and then filtered through Kieselguhr. This solution was added to a stirred slurry of sodium acetylmethylphosphinate (2.9 g, 0.02 mol) in ethanol (20 ml) and the mixture stirred overnight. The solution was evaporated under reduced pressure, giving a white foamy solid which was dissolved in ethanol, precipitated with dry ether and filtered. The filtrate was evaporated to a foamed solid, which was dried in vacuo giving 2.5 g, 58% of product, mp 155°–160°. N.m.r. was consistent with the desired product.

| Analysis: | C | H | N |
|---|---|---|---|
| $C_6H_{13}NNaO_2PS$ requires: | 33.18 | 6.03 | 6.45 |
| Found: | 32.85 | 6.3 | 5.95 |

EXAMPLE 34

Sodium methyl(2-methyl-1,3-diazolidin-2-yl)phosphinate

A solution of sodium acetylmethylphosphinate (2.9 g, 0.02 mol) in ethanol was stirred with ethylene diamine (1.2 g, 0.02 mol) for 28 hours and then evaporated under reduced pressure, giving a powdery white solid. N.m.r. showed this contained no unreacted starting material. Drying under vacuum gave 3.1 g product (83%), which still contained trapped ethanol, but otherwise appeared virtually pure by n.m.r.

EXAMPLE 35

Sodium methyl(2-methyl-1,3-thiazolidin-2-yl)phosphinate

A solution of sodium acetylmethylphosphinate in ethanol was stirred with a solution of 2-aminoethanethiol in ethanol (prepared from the hydrochloride salt (2.3 g, 0.02 mol) and NaOH (0.8 g, 0.02 mol) in ethanol, the precipitated NaCl being filtered off) for 3 days. The mixture was then evaporated under reduced pressure giving a pale yellow solid which was precipitated from ethanol with acetone and the residue triturated with acetone giving a yellow solid, 2.2 g, 54%. Mp (decomp) 140°.

N.m.r was consistent with the desired product.

| Analysis: | C | H | N |
|---|---|---|---|
| $C_5H_{11}NNaO_2PS$ requires: | 29.56 | 5.46 | 6.89 |
| Found: | 26.18 | 6.6 | 5.1 |

EXAMPLE 36

Sodium (2,2-dicyano-1-methylethenyl)methylphosphinate

The compound of Example 8 (6.3 g) and malononitrile (2.0 g) were dissolved in ethanol (150 ml) and the solution was allowed to stand for 18 hours, evaporated in vacuo and the residue triturated with ether. The product was filtered off, washed well with ether and dried to give an orange solid (6.0 g).

The i.r. spectrum supported the required structure and the nmr spectrum showed that no starting material remained.

| Analysis (for monohydrate) | | | |
|---|---|---|---|
| $C_6H_6N_2NaO_2P$ requires: | C 34.28 | H 3.81 | N 13.3% |
| Found: | 34.8 | 3.6 | 12.8 |

The product was purified by dissolution in ethanol (250 ml) and dilution of the solution with ethyl acetate (200 ml) to give a pale yellow powder (3.8 g). Softens at 100° C. begins to decomp at 155° C.

EXAMPLE 37

Sodium acetylmethylphosphinate oxime

Sodium hydroxide (1 2335 g) and hydroxylamine hydrochloride (2.1432 g) were dissolved separately in ethanol (75 ml for each) and the solutions were then mixed and the resulting sodium chloride filtered off. Sodium acetylmethylphosphinate (4.4406 g) was dissolved in ethanol (100 ml) and the solution was added to the solution of hydroxylamine prepared above. The mixture was stirred at room temperature and the oxime began to precipitate immediately. After 17 hours the oxime was filtered off, washed with a little ice cold ethanol and dried. Yield 3.6 g. The product did not melt below 300° C.

| Analysis: | C | H | N |
|---|---|---|---|
| $C_3H_7NNaO_3P$ requires: | 22.65 | 4.44 | 8.81 |
| Found: | 22.8 | 3.95 | 8.4 |

EXAMPLE 38

Sodium acetylmethylphosphinate O-benzyloxime

Procedure as for Example 37 using $C_6H_5CH_2ONH_2HCl$ (4.797 g), sodium hydroxide (1.2037 g) and sodium acetylmethylphosphinate (4.331 g), except that the benzyl ether is less soluble in ethanol than hydroxylamine hydrochloride and was dissolved in 300 ml solvent.

The mixture was allowed to stand for 18 hours (no precipitate appeared) and was then evaporated in vacuo. The residue was triturated with ethanol, a little inorganic material filtered off and the filtrate extracted to give the title compound as a buff coloured deliquiscent solid (7.1 g); n.m.r. supports the required structure. The product softens at 40° C., slowly melts to 55° C. to give a glass.

| Analysis: | C | H | N |
|---|---|---|---|
| $C_{10}H_{13}NNaO_3P$ requires: | 48.2 | 5.26 | 5.62 |
| Found: | 45.1 | 5.85 | 5.07 |
| $C_{10}H_{15}NNaO_4$ Requires: | C 44.95 | H 5.66 | N 5.24% |

EXAMPLE 39

Sodium [1-(N-ethoxyimino)ethyl] methylphosphinate

Sodium acetylmethylphosphinate (3.5 g, 0.024 mole) was added to a solution of methoxyamine hydrochloride (0.024 mole, 2 g) and NaOH (0.96 g) in ethanol (20 ml) and filtered to remove the precipitated NaCl.

The reaction mixture was stirred overnight and the solid precipitate filtered off and dried to yield the title compound, 4.3 g, 96%. Mp (dec) 180°. N.m.r. was consistent with the desired structure.

EXAMPLE 40

Sodium [1-(N-methoxyimino)ethyl]methylphosphinate

Methoxyamine hydrochloride (1.7 g, 0.02 mol) and sodium hydroxide (0.8 g, 0.02 mol) were stirred together in methanol (20 ml) until all the NaOH had dissolved (about ½ hr). The solution was filtered through Keiselguhr and added to a stirred solution of sodium acetylmethylphosphinate (2.6 g, 0.02 mol) in methanol (10 ml). The mixture was stirred overnight at room temperature, and then evaporated, giving a pale yellow solid. This was recrystallised from methanol/ether giving a white solid, 2.5 g, 72% which appears to be mainly one geometrical isomer of the desired product with some of the other (6:1 ratio) by n.m.r. M.P. 230–235 decomp.

| Analysis | C | H | N |
|---|---|---|---|
| $C_4H_9NNaO_3P$ requires: | 27.76 | 5.24 | 8.09 |

| Analysis | C | H | N |
|---|---|---|---|
| Found: | 22.78 | 4.55 | 4.55 |

The mother liquor from the crystallisation was evaporated giving a yellow solid, 0.8 g, 23%. N.m.r. showed this to be an approximately 1:1 mixture of geometrical isomers of the title compound.

EXAMPLE 41

Sodium methyl(1-phenyliminoethyl)phosphinate

A mixture of sodium acetylmethylphosphinate (4.3 g) and aniline (3.2 ml) was dissolved in ethanol (200 ml) and allowed to stand for 72 hours over 4 A molecular sieve. The solution was filtered free of the solid phase, evaporated in vacuo and the residue was triturated with ether to give a pale brown solid (6.1 g). The nmr spectrum showed that the crude product contained an aromatic moiety.

Softens 165° C. gradually decomposes with no sharp melting point.

| | C | H | N |
|---|---|---|---|
| $C_9H_{11}NNaO_2P$ requires: | 49.32 | 5.06 | 6.39 |
| Found: | 45.02 | 5.15 | 5.44 |
| $C_9H_{11}NNaO_2P \cdot H_2O$ requires: | C 45.57; | H 5.49; | N 5.91 |

EXAMPLE 42

Sodium methyl(1-phenylhydrazonoethyl)phosphinate

A solution of sodium acetylmethylphosphonite (4.3 g) and phenylhydrazine (4 ml) in ethanol (100 ml) was stirred for 16 hr and then evaporated in vacuo. The residue was triturated with ether and the solid filtered off and dried in vacuo to give the product as a pale brown deliquescent solid (6.8 g). NMR spectrum was consistent with the required structure. The product softens at 60° C. and slowly decomposes but has no sharp melting point.

| | C | H | N |
|---|---|---|---|
| $C_9H_{14}N_2NaO_2P \cdot H_2O$ requires: | C 42.85; | H 5.55; | N 11.1% |
| Found: | C 42.3; | H 5.82; | N 10.78% |

EXAMPLE 43

Sodium (1-(2,4-dinitrophenylhydrazono)ethyl)methylphosphinate

Sodium acetylmethylphosphinate (4.3 g) and 2,4-dinitrophenylhydrazine (5.9 g) were refluxed and stirred in ethanol (150 ml). After 1 hr the hydrazine had disappeared to be replaced by a yellow solid. The mixture was refluxed and stirred a further hour, cooled and the hydrazone filtered off, washed with a little cold ethanol and dried (8.0 g). The filtrate on evaporation gave residual material (1.4 g).

The main crop was crystallised from ethanol to give the hydrazone as orange crystals (5.8 g); nmr supports the required structure. The compound darkened at 255° C. and did not melt below 280° C.

| Analysis: | C | H | N |
|---|---|---|---|
| $C_9H_{10}N_4NaO_6P$ requires: | 33.34 | 3.11 | 17.29 |
| Found: | 33.72 | 3.29 | 16.96 |

EXAMPLE 44

Sodium acetylmethylphosphinate semicarbazone

Semicarbazide hydrochloride (3.6867 g) was dissolved in water (20 ml) and the solution was diluted with ethanol (50 ml). Sodium hydroxide (1.3231 g) was dissolved in a mixture of ethanol (50 ml) and water (5 ml). The solutions were mixed and a solution of sodium acetylmethylphosphinate (4.7632 g) in ethanol (75 ml) was added. The mixture was stirred overnight and, since no precipitate had appeared, it was evaporated in vacuo. The residue was triturated with ethanol and insoluble material was filtered off. The filtrate was evaporated in vacuo to give the crude semicarbazone which was triturated with acetone and filtered off to give an amorphous colourless solid. On heating the compound softens at 110°, and decomposed at 170° and finally melted at 230°. NMR supports the structure.

EXAMPLE 45

Sodium (1-cyano-1-hydroxyethyl)methylphosphinate

Sodium acetylmethylphosphinate (2.9 g) was dissolved in water (10 ml) and a solution of sodium cyanide (1.0 g) in water (10 ml) was added, followed by sufficient 1 N acid to reduce the pH to 7.0. The resulting solution was stirred for 18 hr, evaporated in vacuo and the residue was triturated with ethanol. Inorganic material was filtered off and the filtrate evaporated in vacuo, re-triturated with ethanol and the procedure repeated. The final residue was triturated with acetone to give the crude cyanohydrin as a deliquescent solid whose nmr was consistant with that of the required product.

The product was crystallised from ethanol/acetone and gave 0.5 g of the cyanohydrin, softens 130°, decomp. 150° C.

| Analysis: | C | H | N |
|---|---|---|---|
| $C_4H_7NNaO_3P$ requires: | 28.08 | 4.12 | 8.19 |
| Found: | 27.81 | 3.84 | 7.70 |

The filtrate was evaporated in vacuo, dissolved in the minimum of ethanol and ether was gradually added to give a second crop of the title compound (0.7 g).

EXAMPLE 46

Sodium (dimethoxymethyl)methyl phosphinate (a) Methyl (dimethoxymethyl)methylphosphinate Methylphosphonous dichloride (10 g, 0.855 mol) was added dropwise, with stirring, under $N_2$ to trimethyl orthoformate (27.2 , 0.256 mol) containing anhydrous $SnCl_2$ (approx 0.1 g) maintaining the temperature as near to −20° C. as possible. The addition was exothermic and took about 15 min during which time a white suspension was formed. After allowing the temperature to rise to room temperature a clear solution was formed and stirring was continued for 2 h.

After leaving the solution overnight under $N_2$ it was distilled in vacuo giving (after a small fore-run) a fraction b.p. 124° at 25 mm Hg. Yield = 8.9 g.

The n.m.r. spectrum was in agreement with the proposed structure.

(b) Sodium (dimethoxymethyl)methylphosphinate

The product of step (a) (7.4 g) in methyl ethyl ketone (75 ml) was refluxed for 2 hr with sodium iodide (7.0 g). The resulting suspension was cooled and the product filtered off, washed and dried (7.4 g). The n.m.r spectrum was consistent with the required material.

| Analysis: | C | H |
|---|---|---|
| $C_4H_{10}NaO_4P$ requires: | 27.28 | 5.72 |
| Found: | 26.89 | 5.36 |

EXAMPLE 47

Sodium formylmethylphosphinate

A solution of sodium (dimethoxymethyl)methylphosphinate (15.7 g) in formic acid (110 ml) containing water (5.5 ml) was stirred at 40°–50° for 36 h. Evaporation of the solvent in vacuo afforded a solid which was suspended in toluene and evaporated to remove any excess formic acid. The residue was triturated with dry ether, filtered, and dried in vacuo over anhydrous $CaCl_2$. N.m.r and i.r spectra of the solid showed it to be the required compound. Yield=10.0 g, m.p 145° (decomp).

| Analysis: | C | H |
|---|---|---|
| $C_2H_4NaO_3P$ requires: | 18.48 | 3.1 |
| Found: | 16.29 | 4.32 |

EXAMPLE 48

Sodium (1,1-dimethoxypropyl)methylphosphinate

Methyl (1,1-dimethoxypropyl)methylphosphinate was prepared from trimethyl ortho-propionate and methylphosphonous dichloride according to the procedure of Example 16. The product boiled at 76° C. at 0.5 mm Hg.

This ester, (15.7 g) was refluxed in methyl ethyl ketone containing sodium iodide (13.2 g). No precipitate appeared and after 4 hr the reaction mixture was evaporated to low volume and diluted with ether to give a gummy product. The solvent was decanted, the residue dissolved in a minimum of acetone and the procedure repeated twice. The final glassy product was dissolved in acetone and the solvent removed in vacuo to give the title product as an amorphous white solid which was extremely deliquescent. Yield 16.4 g. The n.m.r spectrum was consistent with the required product.

EXAMPLE 49

Sodium methyl(1-oxopropyl)phosphinate

The product of Example 48 (13.6 g) was dissolved, with warming on the steam bath in acetic acid (100 ml) containing water (3 ml). The solution was left for 16 hrs and was then worked up as in Example 8(a).

The crude oily material was dissolved in acetone and diluted with ether until no more material precipitated. The precipitate was redissolved in acetone and this procedure was repeated three times. Finally the last portion of solvent was decanted, fresh ether was added and the gum scratched until it solidified. This material was filtered off at the aspirator. The moist solid was rapidly transferred to a dessicator and dried in vacuo to give a brown amorphous solid (5.0 g). The n.m.r spectrum was in agreement with the required structure.

EXAMPLE 50

Dodecylguanidine salt of (1,1-dimethoxyethyl)methylphosphinate

The product of Example 18 (3.8 g) and dodecylguanidine hydrochloride (5.3 g) were dissolved separately in the minimum of ethanol and the solutions mixed. After 16 hrs sodium chloride was filtered off and the filtrate was evaporated in vacuo to give a gummy solid. This was triturated with acetone to give the required salt as an insoluble colourless solid (4.2 g), m.p. 123°–125° C. The n.m.r spectrum was in agreement with the required structure.

| Analysis: | C | H | N |
|---|---|---|---|
| $C_{18}H_{42}N_3O_4P$ requires: | 54.66 | 10.70 | 10.63 |
| Found: | 55.04 | 11.03 | 10.67 |

EXAMPLE 51

Isopropylamine salt of (1,1-dimethoxyethyl)methylphosphinate

By the procedure of Example 50 the product of Example 18 (3.8 g) and isopropylamine hydrochloride (2.0 g) were mixed, and after 16 hrs sodium chloride was removed and the filtrate evaporated in vacuo. The residue was crystallised from acetone to give the isopropylamine salt (1.7 g), softens 110° C., melts 123° C. The n.m.r spectrum supports the required structure.

| Analysis: | C | H | N |
|---|---|---|---|
| $C_8H_{22}NO_4P$ requires: | 42.28 | 9.76 | 6.16 |
| Found: | 42.65 | 9.34 | 5.92 |

EXAMPLE 52

Sodium acetylmethylphosphinate thiosemicarbazone

A mixture of sodium acetylmethylphosphinate (3.5 g) and thiosemicarbazide (2.2 g) was stirred in ethanol (15 ml) for 4 days. The precipitated hydrazone was filtered off and dried (4.6 g). The n.m.r spectrum supports the required structure. The compound slowly decomposes above 125°.

EXAMPLE 53

1,3,5-Tributyl-4-methylamino-1,2,4-triazolium (1,1-dimethoxyethyl)methylphosphinate By the procedure of Example 50 the product of Example 18 (3.8 g) and 1,3,5-tributyl-4-methylamino-1,2,4-triazolium chloride (5.7 g) were mixed and the resulting sodium chloride filtered off. The filtrate was evaporated in vacuo and the residual oil treated with acetone. Unreacted phosphinate (0.3 g) was filtered off and the filtrate evaporated in vacuo, finally at the oil pump, to give the required salt as an amber oil (6.0 g). The nmr spectrum was in agreement with the structure.

| Analysis: | C | H | N |
|---|---|---|---|
| $C_{20}H_{43}N_4O_4P$ requires: | 55.28 | 9.97 | 12.89 |

|Analysis:|C|H|N|
|---|---|---|---|
|Found:|55.29|9.73|13.16|

EXAMPLE 54

1-Butyl-4-butylamino-3,5-dipropyl-1,2,4-triazolium (1,1-dimethyloxyethyl)methylphosphinate By the procedure of Example 53 the product of Example 18 (3.8 g) and 1-butyl-4-butylamino-3,5-dipropyl-1,2,4-triazolium chloride (6.0 g) were mixed and the reaction worked up to give the rquired salt as a pale yellow oil (6.5 g). The nmr spectrum was in agreement with the required structure.

|Analysis:|C|H|N|
|---|---|---|---|
|$C_{21}H_{45}N_4O_4P$ requires:|56.22|10.11|12.49|
|Found:|55.78|9.78|12.23|

EXAMPLE A

Seeds of the following species were sown in John Innes I potting compost contained in anodised aluminium pans 190 mm long×95 mm wide×50 mm deep:
 Peas—*Pisum sativum*
 Mustard—*Sinapis alba*
 Linseed—*Linum usitatissimum*
 Ryegrass—*Lolium perenne*
 Sugarbeet—*Beta vulgaris*
 Oats—*Avena sativa*
 French beans—*Phaseolus vulgaris*

The seeds were watered and placed in a controlled environment room at 22° C., 65–85% relative humidity and 14 hours per day artificial illumination at 13,000 lux. After 14 days the seedlings received foliar sprays of the test compounds formulated as an aqueous suspension or solution containing 1,000 ppm of the wetting agent Lissapol NX.

The concentrations of active ingredients and volume of application were adjusted so as to give rates of 11.2, 2.8 and 0.7 kg per hectare of active ingredient in 450 liters per hectare. The plants were returned to the controlled environment room. After 21 days they were visually assessed for herbicidal effects compared with unsprayed controls. All differences from controls are given as percentage supression in the table below.

| Compound of Example | POST EMERGENT HERBICIDAL RESULTS AFTER 21 DAYS | | | | | | | | | | | | | | | | | | | | |
|---|---|---|---|---|---|---|---|---|---|---|---|---|---|---|---|---|---|---|---|---|---|
| | Peas | | | Mustard | | | Linseed | | | Ryegrass | | | Oats | | | Sugarbeet | | | French beans | | |
| Dose | 0.7 | 2.8 | 11.2 | 0.7 | 2.8 | 11.2 | 0.7 | 2.8 | 11.2 | 0.7 | 2.8 | 11.2 | 0.7 | 2.8 | 11.2 | 0.7 | 2.8 | 11.2 | 0.7 | 2.8 | 11.2 kg/ha |
| 1 | — | 5 | 20 | — | 20 | 70 | — | 40 | 70 | — | 40 | 70 | — | 20 | 60 | — | 30 | 40 | — | 30 | 50 |
| 8 | 5 | 5 | — | 80 | 100 | — | 50 | 100 | — | 80 | 90 | — | 40 | 90 | — | 40 | 50 | — | 30 | 80 | — |
| 17 | 0 | 5 | — | 80 | 100 | — | 90 | 100 | — | 70 | 100 | — | 50 | 90 | — | 70 | 80 | — | 80 | 100 | — |
| 39 | — | — | 5 | — | — | 100 | — | — | 90 | — | — | 90 | — | — | 30 | — | — | 70 | — | — | 70 |
| 44 | — | 0 | 0 | — | 70 | 100 | — | 60 | 100 | — | 40 | 90 | — | 40 | 60 | — | 40 | 80 | — | 40 | 50 |
| 34 | — | 0 | 5 | — | 50 | 100 | — | 50 | 100 | — | 40 | 80 | — | 5 | 40 | — | 20 | 90 | — | 30 | 80 |
| 35 | — | 5 | 15 | — | 100 | 100 | — | 100 | 100 | — | 100 | 100 | — | 40 | 70 | — | 80 | 100 | — | 90 | 80 |
| 45 | — | 5 | 5 | — | 100 | 100 | — | 100 | 100 | — | 100 | 100 | — | 50 | 70 | — | 70 | 90 | — | 40 | 90 |
| 37 | — | 0 | 0 | — | 60 | 100 | — | 70 | 90 | — | 30 | 60 | — | 5 | 30 | — | 60 | 70 | — | 40 | 70 |
| 24 | — | 10 | 50 | — | 70 | 100 | — | 40 | 90 | — | 70 | 80 | — | 40 | 70 | — | 40 | 60 | — | 50 | 60 |
| 15 | — | 10 | 25 | — | 40 | 90 | — | 70 | 90 | — | 40 | 80 | — | 30 | 50 | — | 30 | 40 | — | 40 | 50 |

EXAMPLE B

Seeds of the following species were sown in John Innes I potting compost contained in anodised aluminim pans 190 mm long×95 mm wide×50 mm deep:
 Pale persicaria—*Polygonum Lapathefolium*
 Pigweed—*Amaranthus Retroflexus*
 Wheat—*Triticum aestivum*
 Barley—*Hordeum vulgare*
 Wild Oats—*Avena fatua*
 Blackgrass—*Alopecurus myosuroides*
 Barnyardgrass—*Echinochloa crus-galli*
 Crabgrass—*Digitaria sanguinalis*
 Couch grass—*Agropyron repens*
 Purple nutsedge—*Cyperus rotundus*
 Yellow nutsedge—*Cyperus esculentus*
 Johnson grass—*Sorghum halepense*

The seeds were watered and placed in a controlled environment room at 22° C., 65–85% relative humidity and 14 hours per day artificial illumination at 17,000 lux. After 21 days the seedlings received foliar sprays of the test compounds formulated as an aqueous solution containing 2,000 ppm of the wetting agent Lissapol NX.

The plants were returned to the controlled environment. After 14 days they were visually assessed for herbicidal effects compared with unsprayed controls. All differences from controls were scored in the same way as in Example A. The results are tabulated below:

| Compound of Example | POST EMERGENT HERBICIDAL RESULTS AFTER 21 DAYS | | | | | | | | | | | | | | | | | |
|---|---|---|---|---|---|---|---|---|---|---|---|---|---|---|---|---|---|---|
| | Pale Persicaria | Pigweed | Wheat | | Barley | | Wild Oats | | Blackgrass | | Barnyard grass | | Crabgrass | | Couch grass | Purple Nutsedge | Yellow Nutsedge | Johnson grass |
| | Dose kg/ha | | | | | | | | | | | | | | | | | |
| | 1.4 | 1.4 | 1.4 | 2.8 | 1.4 | 2.8 | 1.4 | 2.8 | 1.4 | 2.8 | 1.4 | 2.8 | 1.4 | 2.8 | 1.4 | 1.4 | 1.4 | 1.4 |
| 1 | — | — | — | 30 | — | 30 | — | 30 | — | 20 | — | 20 | — | 30 | — | — | — | — |
| 8 | 80 | 100 | 50 | 65 | 65 | 100 | 60 | 90 | 70 | 100 | 100 | 100 | 100 | 100 | 50 | 40 | 50 | — |
| 17 | — | — | 70 | — | 100 | — | 70 | — | 70 | — | 100 | — | 100 | — | 100 | 90 | 70 | 100 |
| 45 | — | — | 60 | — | 50 | — | 60 | — | 60 | — | 100 | — | 100 | — | 40 | 40 | 70 | 100 |

-continued

POST EMERGENT HERBICIDAL RESULTS AFTER 21 DAYS

| Compound of Example | Pale Persicaria | Pigweed | Wheat | | Barley | | Wild Oats | | Blackgrass | | Barnyard grass | | Crabgrass | | Couch grass | Purple Nutsedge | Yellow Nutsedge | Johnson grass |
|---|---|---|---|---|---|---|---|---|---|---|---|---|---|---|---|---|---|---|
| | | | | | | | | | | Dose kg/ha | | | | | | | | |
| | 1.4 | 1.4 | 1.4 | 2.8 | 1.4 | 2.8 | 1.4 | 2.8 | 1.4 | 2.8 | 1.4 | 2.8 | 1.4 | 2.8 | 1.4 | 1.4 | 1.4 | 1.4 |
| 44 | — | — | 60 | — | 70 | — | 15 | — | 30 | — | 90 | — | 90 | — | — | — | — | 90 |
| 35 | — | — | 70 | — | 90 | — | 30 | — | 70 | — | 100 | — | 100 | — | 20 | 30 | 40 | 100 |

EXAMPLE C

The compound under test formulated as an attaclay/sand dust was incorporated in John Innes I potting compost at a rate equivalent to 26 parts per million weight/volume of active ingredient to soil and placed in anoidised aluminium pans, 19 cm long×9.5 cm wide×5.0 cm deep. This rate is approximately equivalent to a soil surface application of 11.2 kg active ingredient/hectare cultivated to a depth of 5 cm. Seeds of Peas, Mustard, Linseed, Maize, Oats and Ryegrass were sown in the treated soil, watered and placed in a controlled environment room (22° C., 65–85% relative humidity, 14 hours artificial illumination at 1200 foot candles) for 21 days.

The plants were then visually assessed for any growth regulatory or herbicidal effects. All differences from an untreated control were scored as in Example A.

The results relating to compounds of Examples 8, 17 and 45 are summarised in the following table:

| Species | Example 8 | Example 17 | Example 45 |
|---|---|---|---|
| Peas - (Pisum sativum) | 0 | 15 | 50 |
| Mustard - (Sinapis alba) | 80 | 90 | 80 |
| Linseed - (Linum usitatissimum) | 80 | 90 | 90 |
| Maize - (Zea mays) | 40 | 70 | 80 |
| Oats - (Avena sativa) | 20 | 70 | 90 |
| Ryegrass - (Lolium perenne) | 60 | 100 | 100 |

EXAMPLE D

The procedure of Example B was repeated using the compound of Example 17 and with the difference that the plants were assessed after 28 days.

The results are given below:

| Species | Dosage rate Kg/ha | | |
|---|---|---|---|
| | 2.8 | 1.4 | 0.7 |
| Wheat | — | 70 | 50 |
| Barley | — | 100 | 100 |
| Wild oats | — | 75 | 40 |
| Blackgrass | — | 100 | 50 |
| Barnyardgrass | — | 100 | 100 |
| Crabgrass | — | 100 | 100 |
| Purple nutsedge (Cyperus rotundus) | 100 | 90 | — |
| Yellow nutsedge (Cyperus esculentus) | 90 | 90 | — |
| Couch (Agropyron repens) | 100 | 100 | — |

EXAMPLE E

Aqueous acetone solutions of the compound of Example 15 containing 2000 parts per million (ppm) wt/vol together with 125 ppm of a suitable wetting agent were applied to the soil surrounding the roots and leaves of rice plants having two fully expanded leaves, and wheat plants with one fully expanded leaf. The treated plants, together with controls treated with wetting agent alone, were innoculated 24 hours after the chemical application with an aqueous suspension of spores of the disease organisms known as rice blast, *Pyricularia oryzae* and wheat brown rust, *Puccina recondita* respectively.

The plants were then placed in an atmosphere of 100% humidity for the rice plants at 28° C. until the disease incidence was measured seven days later, and for wheat plants for 24 hours and then transferred to a controlled environment room (18° C. and 80–90% RH) until disease incidence was measured after 12 days, when it was found that the treatments had given 90% disease reduction of both diseases in comparison with less than 5% on the controls.

EXAMPLE F

Aqueous acetone solutions of the compound of Example 1 containing 2000 parts per million (ppm) wt/vol together with 125 ppm of a suitable wetting agent were applied to the foliage and soil surrounding the roots of potato plants having seven fully expanded leaves and barley plants with one fully expanded leaf. The treated plants, together with controls treated with wetting agent alone, were inoculated 24 hours after the chemical application with an aqueous suspension of sporangia and spores respectively of the disease organisms known as potato blight, *Phytophthora infestans* and barley powdery mildew, *Erysiphe graminis*. The plants were then placed in an atmosphere of 100% humidity for 24 hours and then transferred to a controlled environment room (18° C. and 80–90% RH) until disease incidence was measured after five days for potatoes and 10 days for barley when it was found that the treatments had given 80% control of each disease in comparison with less than 5% on the untreated controls.

EXAMPLE G

Aqueous acetone solutions of the compound of Example 17 containing 2000 and 500 parts per million (ppm) wt/vol together with 125 ppm of a suitable wetting agent were applied to the leaves of barley plants with one fully expanded leaf. The treated plants, together with controls treated with wetting agent alone, were inoculated 24 hours after the chemical application with an aqueous suspension of spores of the disease organism known as barley powdery mildew, *Erysiphe graminis*. The plants were then placed in an atmosphere of 100% humidity for 24 hours and then transferred to a controlled environment room (18° C. and 80–90% RH) until disease incidence was measured after 10 days when it was found that the treatments at 2000 and 500 ppm had given 95 and 90% disease reduction respectively in comparison with less than 5% on the untreated controls.

EXAMPLE H

Aqueous acetone solutions of the compound of Example 19 containing 125 parts per million (ppm) wt/vol together with 125 ppm of a suitable wetting agent were applied to the leaves of vine plants having five fully expanded leaves. The treated plants, together with controls treated with wetting agent alone, were inoculated 24 hours after the chemical application with an aqueous suspension of sporangia of the disease organism known as vine downy mildew, *Plasmopara viticola*. The plants were then placed in an atmosphere of 80% humidity, at 14°–18° C. until the disease incidence was measured twelve days later when it was found that the treatments at 125 ppm had given 90% control respectively in comparison with less than 5% on the controls.

We claim:

1. A compound of the formulae:

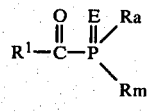

or

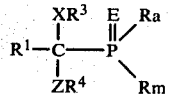

in which Ra represents hydrogen, alkyl, alkenyl, alkynyl or aryl; the alkyl, alkenyl, alkynyl or aryl optionally being substituted by one or more of halogen, alkoxy, alkyl, —$CF_3$ or carboxylic acid or a salt, ester or amide thereof, E is oxygen or sulphur, Rm is —$O^{\ominus}M^{\oplus}$, $M^{\oplus}$ is one equivalent of an agriculturally acceptable cation, $R^1$ represents hydrogen, alkyl, alkenyl, alkynyl or aryl; the alkyl, alkenyl, alkynyl or aryl optionally being substituted by one or more of halogen, alkoxy, alkyl, —$CF_3$ or carboxylic acid or a salt, ester or amide thereof, and X and Z, which may be the same or different, each represent oxygen, sulphur or a group —$NR^5$—, $R^5$ represents hydrogen, alkyl, or aryl, $R^3$ and $R^4$, which may be the same or different each represent alkyl, or aryl each of which may optionally be substituted by hydroxy, alkoxy, alkyl, halogen, carbonyl oxygen or alkoxycarbonyl; or $R^3$ and $R^4$ together form alkylene, or arylene each of which may optionally be substituted by hydroxy, alkoxy, alkyl, halogen, carbonyl oxygen or alkoxycarbonyl, or $XR^3$ and $ZR^4$ together form carbonyl oxygen =$C(CN)_2$ or =$NR^{10}$ in which $R^{10}$ represents alkoxy C 1 to 6, benzyloxy, hydroxy, phenyl, —NH phenyl, —NH—(2,4-dinitrophenyl), —$NHCONH_2$ or —$NHCSNH_2$, or one of $XR^3$ and $ZR^4$ is —OH (or esters or ethers thereof) and the other is —CN or —$SO_3^{\ominus}M^{\oplus}$, $XR^3$ and $ZR^4$ each containing up to and including 10 carbon atoms.

2. A compound according to claim 1, wherein $M^{\oplus}$ is sodium.

3. A compound according to claim 1, wherein Ra is hydrogen or methyl.

4. A compound according to claim 1, wherein $R^1$ is hydrogen, alkyl C 1 to 3, or —$CH_2CH_2COOH$ or a salt or C 1 to 6 alkyl ester thereof, Ra is hydrogen, alkyl C 1 to 6, phenyl, and $M^{\oplus}$ is sodium or lithium.

5. A compound according to claim 1, wherein $R^1$ is methyl or —$CH_2CH_2COOH$ or a salt or C 1 to 6 alkyl ester thereof, Ra is methyl and $M^{\oplus}$ is sodium.

6. A compound according to claim 1 which is sodium acetylmethylphosphinate.

7. A compound according to claim 1 which is sodium (1,1-dimethoxyethyl)-methylphosphinate.

8. A compound according to claim 1 which is a salt of (1,1-dimethoxyethyl)-methylphosphinate.

9. A pesticidal composition which comprises a compound of the formulae:

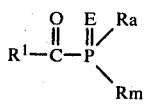

or

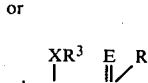

in which Ra represents hydrogen, alkyl, alkenyl, alkynyl or aryl; the alkyl, alkenyl, alkynyl or aryl optionally being substituted by one or more of halogen, alkoxy, alkyl, —$CF_3$ or carboxylic acid or a salt, ester or amide thereof, E is oxygen or sulphur, Rm is —$O^{\ominus}M^{\oplus}$, $M^{\oplus}$ is one equivalent of an agriculturally acceptable cation, $R^1$ represents hydrogen, alkyl, alkenyl, alkynyl or aryl; the alkyl, alkenyl, alkynyl or aryl optionally being substituted by one or more of halogen, alkoxy, alkyl, —$CF_3$ or carboxylic acid or a salt, ester or amide thereof, and X and Z, which may be the same or different, each represent oxygen, sulphur or a group —$NR^5$—, $R^5$ represents hydrogen, alkyl, or aryl, $R^3$ and $R^4$, which may be the same or different each represent alkyl, or aryl each of which may optionally be substituted by hydroxy, alkoxy, alkyl, halogen, carbonyl oxygen or alkoxycarbonyl; or $R^3$ and $R^4$ together form alkylene, or arylene each of which may optionally be substituted by hydroxy, alkoxy, alkyl, halogen, carbonyl oxygen or alkoxycarbonyl, or $XR^3$ and $ZR^4$ together form carbonyl oxygen =$C(CN)_2$ or =$NR^{10}$ in which $R^{10}$ represents alkoxy C 1 to 6, benzyloxy, hydroxy, phenyl, —NH phenyl, —NH—(2,4-dinitrophenyl), —$NHCONH_2$ or —$NHCSNH_2$, or one of the $XR^3$ and $ZR^4$ is —OH (or esters or ethers thereof) and the other is —CN or —$SO_3^{\ominus}M^{\oplus}$, $XR^3$ and $ZR^4$ each containing up to and including 10 carbon atoms in admixture with a carrier or a surface active agent.

* * * * *